United States Patent [19]

Casey et al.

[11] Patent Number: 5,627,056
[45] Date of Patent: May 6, 1997

[54] METHOD OF SYNTHESIZING LIPIDS AND COSMETIC COMPOSITION COMPRISING THEM

[75] Inventors: John Casey, Wellingborough; Peter S. Cheetham, Harrold; Peter C. Harries, Risely; Della Hyliands, St. James; John T. Mitchell, Bedford, all of United Kingdom; Anthony V. Rawlings, Wyckoff, N.J.

[73] Assignee: Elizabeth Arden Co., Division of Conopco, Inc., New York, N.Y.

[21] Appl. No.: 386,140

[22] Filed: Feb. 9, 1995

Related U.S. Application Data

[62] Division of Ser. No. 146,550, Nov. 2, 1993, abandoned.

[30] Foreign Application Priority Data

| | | | |
|---|---|---|---|
| Nov. 3, 1992 | [GB] | United Kingdom | 9223001 |
| Apr. 3, 1993 | [GB] | United Kingdom | 9306973 |
| Aug. 10, 1993 | [GB] | United Kingdom | 9316629 |

[51] Int. Cl.⁶ ............... C12P 7/64; C12N 1/00; C12N 1/14
[52] U.S. Cl. ........... 435/134; 435/128; 435/129; 435/930; 554/35; 554/40; 554/41; 554/42; 554/69; 424/401
[58] Field of Search ........... 424/401; 435/134, 435/128, 129, 930; 554/35, 40–42, 69

[56] References Cited

U.S. PATENT DOCUMENTS

| | | | |
|---|---|---|---|
| 4,275,162 | 6/1981 | Beppu | 435/196 |
| 4,782,019 | 11/1988 | Kokusho | 435/89 |
| 4,950,688 | 8/1990 | Bowser et al. | 514/847 |
| 5,198,210 | 3/1993 | Critchley et al. | 424/78.03 |
| 5,202,357 | 4/1993 | Bowser et al. | 514/847 |
| 5,326,565 | 7/1994 | Critchley et al. | 424/401 |

FOREIGN PATENT DOCUMENTS

| | | |
|---|---|---|
| 0097059 | 12/1983 | European Pat. Off. |
| 0482860 | 4/1992 | European Pat. Off. |
| 2178312 | 2/1987 | United Kingdom |
| 2213723 | 8/1989 | United Kingdom |
| WO94/26919 | 11/1994 | WIPO |
| WO95/11881 | 5/1995 | WIPO |

OTHER PUBLICATIONS

International Search Report in International Patent Application No. PCT/GB 93/02230.

Pascher, I., "Synthesis of Galactosylphytosphingosine and Galactosyl–ceramides Containing Phytosphingosine", *Chemistry and Physics of Lipids*, vol. 12, (1974), pp. 303–315.

Stodola, F. et al., "Formation of Extracellular Sphingolipids by Microorganisms", *The Journal of Biological Chemistry*, vol. 235, No. 9, Sep. 1960, pp. 2584–2585.

Wickerham, L. et al., "Formation of Extracellular Sphingolipides by Microorganisms", *Journal of Bacteriology*, vol. 80, (1960), pp. 484–491.

Green, M. et al., "Studies on the Production of Sphingolipid Bases by the Yeast, Hansenula Ciferri", *Biochimica et Biophysica ACTA, Lipids and Lipid Metabolism*, vol. 98, (1965), pp. 582–588.

Data Brochure—"Yeast Derived Ceramides". Gist–Brocades, Apr. 1992.

*Primary Examiner*—Gollamudi S. Kishore
*Attorney, Agent, or Firm*—Rimma Mitelman

[57] ABSTRACT

An efficient method of producing phytosphingosine-containing ceramide one comprising: (a) obtaining a phytosphingosine base from tetraacetylphytosphingosine (TAPS) by a deacetylation reaction wherein the TAPS is produced by fermentation of cells of the F-60-10 mating type strain of *Hansenula ciferrii* using a fed-batch mode and a non-fermentable carbon source; and (b) coupling together the phytosphingosine base and a fatty acid/ω-hydroxy fatty acid component wherein the ω-hydroxy fatty acid component is prepared by a process which includes Kolbé synthesis.

7 Claims, 5 Drawing Sheets

METHOD OF SYNTHESIZING LIPIDS AND COSMETIC COMPOSITION COMPRISING THEM

This is a divisional of U.S. application Ser. No. 08/146,550, filed Nov. 2, 1993, now abandoned.

FIELD OF THE INVENTION

This invention relates to a method of synthesising phytosphingosine-containing ceramide one structures plus cosmetic compositions comprising these structures.

BACKGROUND TO THE INVENTION

Ceramides are an important group of lipids, members of which are found in the epidermis of mammals. Skin ceramides are believed to play an important role in the water permeability properties of the skin, providing an epidermal water-barrier which functions to give increased strength to the skin structure and to decrease water loss and so improve the condition of the skin.

Ceramides are N-acylated sphingosine bases. Sphingosine bases are of variable chain length and have the general formula (i):

$$CH_3(CH_2)_x ACHOHCH(NH_2)CH_2OH \quad \text{(i)}$$

where A is —CH=CH— (sphingosine), —CH$_2$CHOH— (phytosphingosine) or —CH$_2$CH$_2$— (dihydrosphingosine), and where x is generally in the broad range 7 to 27, more typically in the range 10 to 16. It should be noted that sphingosines contain asymmetric carbon atoms and so various stereoisomers are possible. Sphingosine/ceramides from especially mammalian sources are all the D-erythro isomer and phytosphingosine/phytoceramides the D-D-erythro isomer. Seven distinguishable groups of ceramides have been identified in pig and human epidermis. Each group consists of molecules of varying fatty acid chain length. The structures of typical skin ceramides are described in the paper entitled "Ceramides of Pig Epidermis: Structure Determination" by P. W. Wertz and D. T. Downing in Journal of Lipid Research, Vol 24, 1983, pages 759–765.

Because of their properties it is known to use ceramides, ceramide derivatives and also pseudoceramides (synthetic molecules which have properties similar to those of naturally occurring ceramides) as components of skin care compositions.

It is difficult to extract ceramides from natural sources, and in some cases the resulting product is not acceptable for cosmetic compositions. Furthermore, ceramides are difficult and expensive to synthesise chemically.

It has been proposed in EP 0 097 059 to synthesise N-[omega-(O-linoleoyl) 23-cis-dotriacontenoyl] sphingosine by chemically synthesising an appropriate sphingosine component and linking this to an appropriate acid.

The paper "Formation of Extracellular Sphingolipids by Microorganisms" by H. G. Maister et. al. in Appl Microbiol vol 10, page 401 to 406 describes a process for producing tetraacetyl phytosphingosine (TAPS) from the F-60-10 mating type strain of the yeast *Hansenula ciferrii*. This process uses glucose as a carbon source in a batch mode fermentation at 25° C. The process, however, is not very efficient, and while it can yield sufficient TAPS for experimental purposes the yield is too low to be practicable for commercial purposes. The TAPS produced is the D-D-erythro isomer, the same as occurs in human skin.

The present inventors have derived a modified process for producing TAPS from *Hansenula ciferrii* that is much more efficient and which is then used as a component of commercial production of phytosphingosine-containing ceramide one.

DISCLOSURE OF THE INVENTION

Accordingly the present invention provides a method of producing a phytoshingosine-containing ceramide one having the general structure (1):

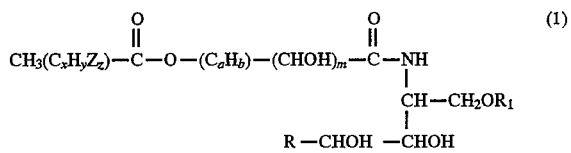

where

R represents a linear or branched, saturated or unsaturated, hydroxylated or non-hydroxylated aliphatic hydrocarbon having from 8 to 28 carbon atoms;

R$_1$ represents H, a phosphate residue, a sulphate residue or a sugar residue

Z is —OH or an epoxy oxygen a is an integer of from 7 to 50 b is an integer of from 10 to 100 m is 0 or 1 x is an integer of from 12 to 20 y is an integer of from 20 to 40 z is 0 or an integer of from 1 to 4 comprising:

(a) obtaining a phytoshingosine base from TAPS by a deacetylation reaction wherein the TAPS is produced by fermentation of cells of the F-60-10 mating type strain of *Hansenula ciferrii* using a fed-batch mode and a non-fermentable carbon source; and (b) coupling together the phytosphingosine base and a fatty acid/hydroxy fatty acid component having the general structure (2) via an amide linkage:

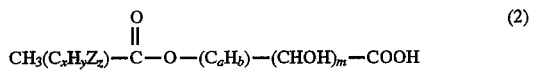

where

Z is —OH or an epoxy oxygen a is an integer of from 7 to 50 b is an integer of from 10 to 100 m is 0 or 1 x is an integer of from 12 to 20 y is an integer of from 20 to 40 z is 0 or an integer of from 1 to 4 wherein the fatty acid/hydroxy fatty acid component having the general structure (2) is prepared by linking together an ω-hydroxy fatty acid having the structure (3)

and a fatty acid having the general structure (4)

the ω-hydroxy fatty acid (3) being prepared by a process which includes Kolbé synthesis.

The present invention also provides a method of producing a fatty acid/ω-hydroxy acid component having the general structure (2):

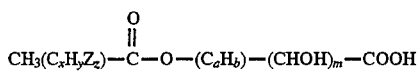  (2)

where
Z is —OH or an epoxy oxygen
a is an integer of from 7 to 50
b is an integer of from 10 to 100
m is 0 or 1
x is an integer of from 12 to 20
y is an integer of from 20 to 40
z is 0 or an integer of from 1 to 4
wherein an ω-hydroxy fatty acid having the structure (3):

  (3)

is linked to a fatty acid having the general structure (4):

  (4)

the ω-hydroxy fatty acid (3) being prepared by a process which includes Kolbé synthesis.

Preferably the fermentation of *Hansenula ciferrii* to produce TAPS is conducted at 30° C.

Surprisingly, the inventors have discovered that yields are further increased when the fermentation of *Hansenula ciferrii* is carried out in the presence of a solvent selected from ethanol, methanol and mixtures thereof. The fermentation is therefore preferably conducted in the presence of such solvents.

Additionally yields are noted to be improved when the fermentation of *Hansenula ciferrii* is carried out in the presence of a surfactant.

Examples of suitable surfactants are Tween and Triton. The fermentation is therefore preferably conducted in the presence of such surfactants.

Furthermore, yields are noted to be improved when the fermentation of *Hansenula ciferrii* is carried out in the presence of selected precursors e.g. palmitic acid, serine and mixtures thereof. The fermentation is therefore preferably conducted in the presence of such precursors.

Preferably the non-fermentable carbon source is glycerol. Use of a non-fermentable carbon source improves the biomass titres (g cells/liter fermentation broth) and hence the productivity of the reaction (eg TAPS/liter). TAPS is conveniently extracted from the fermentation products by solvent extraction.

The fermentation process produces a mixture of products, namely phytosphingosines with some sphingosines, of mixed chain lengths. The main product is TAPS, with some triacetylphytosphingosine and also some triacetylsphingosine. The products are a mixture of $C_{16-20}$ of odd and even chain length, mainly straight chain but possibly with some branched chain products. The main product is $C_{18}$ straight chain TAPS.

TAPS can be readily converted to phytosphingosine by a suitable deacetylation reaction, as is well known to those skilled in the field, e.g. by base catalysed hydrolysis for example using potassium hydroxide.

The phytosphingosine obtained via fermentation of *Hansenula ciferrii* is then used for the preparation of phytosphingosine-containing ceramide one. The use of phytosphingosine obtained by fermentation for this preparation is particularly advantageous to the use of other sources of phytosphingosine (e.g. chemically synthesised) because the phytosphingosine obtained by fermentation is the D-D-erythro isomer, the same as occurs in human skin. Other methods of preparation of phytosphingosine produce a mixture of stereoisomers which must be separated prior to use. Accordingly use of phytosphingosine obtained by fermentation for the preparation of ceramide one provides a very simple, cost effective method.

Alpha hydroxy fatty acids are also produced in the fermentation reaction. The acids are produced in a range of chain lengths from about $C_{16-24}$. The amount of acids produced can be controlled by varying the carbon source: more is produced from glucose than glycerol. The acids can be separated and used in the production of component (2) for production of ceramide one.

The fatty acid/hydroxy fatty acid component of ceramide one has the general structure (2) shown above. Component (2) can be produced by esterifying ω-hydroxy acid with fatty acid or fatty acyl chloride.

Synthesis of ω-hydroxy fatty acid of suitable chain length can be effected, for example, by using Kolbé synthesis to link together the half esters of two dioic acids, to produce the diester of a longer chain dioic acid. After hydrolysis to the half ester the molecule can then be reduced to produce an omega hydroxy long chain fatty acid. The two dioic acids used can be the same or different. For example, two $C_{16}$ dioic acids can be linked to form a $C_{30}$ acid, two $C_{12}$ dioic acids can be linked to form a $C_{22}$ acid, etc. The reaction scheme is shown in FIG. 4.

Alternatively, a dioic acid half ester can be linked to an ω-hydroxy monocarboxylic acid by Kolbé synthesis to produce a longer chain ω-hydroxy acid. For example $C_{16}$ dioic acid half ester and $C_{16}$ omega hydroxy monocarboxylic acid produce $C_{30}$ omega hydroxy acid.

Alternatively two ω-hydroxy fatty acids may be coupled to give a long chain diol, followed by partial oxidation to give a long chain ω-hydroxy fatty acid.

The long chain fatty acid/ω-hydroxy fatty acid component (2) of ceramide 1 can be made in a two stage process, for example by first linking two $C_{16}$ dioic (dicarboxylic) acid half esters followed by reduction to produce a $C_{30}$ omega hydroxy acid and then linking linoleic acid (which is commercially available, e.g. derived from plant oil such as sunflower oils) by an esterification reaction to produce the long chain acid. The linoleic acid is preferably activated, for example, in the form of an acyl chloride.

It will thus be seen that this approach is very versatile and can enable production of a wide range of long chain fatty acid/ω-hydroxy fatty acid components of general structure (2).

Kolbé synthesis reactions are well known to those skilled in the art, and details will not be given here.

Dioic acids are conveniently obtained by biochemical oxidation of monocarboxylic fatty acids, e.g. using *Candida cloacae*, for example as disclosed in EP 0 341 796.

The phytosphingosine base and fatty acid component/hydroxy fatty acid (2) can be readily linked by chemical or enzymic routes, e.g. using conventional N acylation reactions.

For example, a simple amidation reaction can be carried out, possibly acid or base catalysed or possibly non-catalysed after carboxyl group activation. For instance, the fatty acid component can be converted to the methyl ester and reacted, under vacuum with heating, with the phytosphingosine base and sodium methoxide catalyst. This reaction is found to be simple, straightforward and effective, giving a good yield of product, and furthermore does not require the presence of a solvent.

Component (2) may alternatively be reacted in the form of the acid chloride or using an activating reagent such as 2-chloromethyl pyridium iodide.

Enzymic routes are also possible.

The order of reaction steps is not critical. For example a component (2) may be synthesised from shorter components, as described above, and then coupled to the phytosphingosine base. Alternatively, a ω-hydroxy fatty acid component may be linked to the phytosphingosine base prior to esterification of the ω-hydroxyl group.

It will be apparent that the invention provides the potential for production of a wide range of phytosphingosine-containing ceramide one structures, both identical to those found in nature and of novel structure.

In a further aspect, the present invention provides a phytosphingosine-containing ceramide one produced by the method of the invention, and derivatives thereof.

The phytosphingosine-containing ceramide one structures find particular application in the treatment of skin, hair and nails.

In a further aspect, the invention thus provides a cosmetic composition suitable for topical application to skin, hair or nails comprising:

(i) an effective amount of from 0.00001 to 50% by weight of a phytosphingosine-containing ceramide one having the general structure (1):

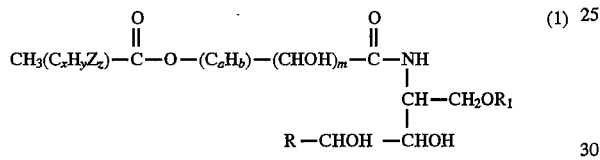

where R represents a linear or branched, saturated or unsaturated, hydroxylated or non-hydroxylated aliphatic hydrocarbon having from 8 to 28 carbon atoms;

$R_1$ represents H, a phosphate residue, a sulphate residue or a sugar residue

Z is —OH or an epoxy oxygen a is an integer of from 7 to 50 b is an integer of from 10 to 100 m is 0 or 1 x is an integer of from 12 to 20 y is an integer of from 20 to 40 z is 0 or an integer of from 1 to 4 wherein the phytoshingosine-containing ceramide one is synthesised according to the invention; and (ii) a cosmetically acceptable vehicle for the phytosphingosine-containing ceramide one.

With reference to structure (1) the group R preferably represents an aliphatic hydrocarbon group having from 12 to 22 carbon atoms.

With reference to structure (1), the value of "a" is preferably an integer of from 24 to 30 and the value of "b" is preferably an integer of from 44 to 60.

Structure (4) preferably represents a straight chain saturated $C_{16-18}$, fatty acid residue or a straight chain all cis n-6,9 di-unsaturated $C_{16-18}$ fatty acid residue.

Specific examples of these phytosphingosine-containing ceramide one structures are those having the structures (5) to (10):

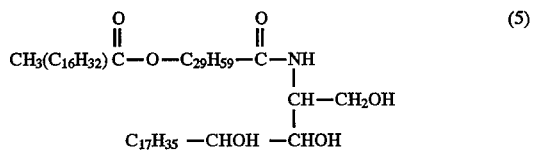

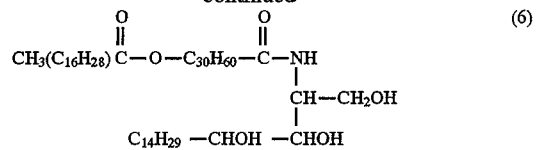

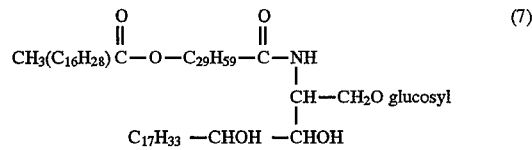

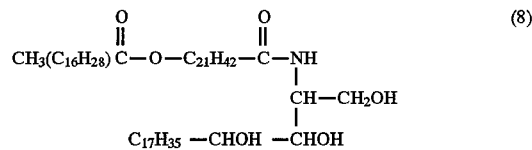

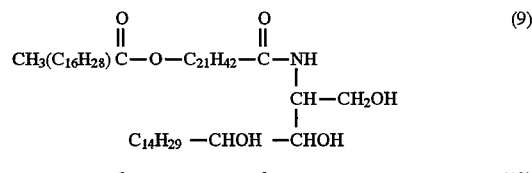

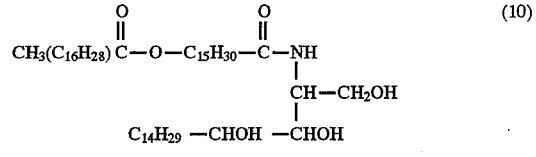

The amount of the phytosphingosine-containing ceramide one present in the composition according to the invention is from 0.00001 to 50%, preferably from 0.001 to 20% and most preferably from 0.1 to 10% by weight.

THE COSMETICALLY ACCEPTABLE VEHICLE

The composition according to the invention also comprises a cosmetically acceptable vehicle to act as a dilutant, dispersant or carrier for the phytosphingosine-containing ceramide one, so as to facilitate its distribution when the composition is applied to the skin and/or hair.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, glyceryl monostearate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, passion flower oil, palm kernel oil, rapeseed oil, safflower seed oil, evening primrose oil, soybean oil, sunflower seed oil, avocado oil, olive oil, sesame seed oil, coconut oil, arachis oil, castor oil, acetylated lanolin alcohols, petroleum jelly, mineral oil, butyl myristate, isostearic acid, palmitatic acid, isopropyl linoleate, lauryl lactate, myristyl lactate, decyl oleate, myristyl myristate;

Propellants, such as air, propane, butane, isobutane, dimethyl ether, carbon dioxide, nitrous oxide;

Solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the emulsion, and can, in the absence of other cosmetic adjuncts, form the balance of the composition.

OPTIONAL SKIN BENEFIT MATERIALS AND COSMETIC ADJUNCTS

A particularly convenient form of the composition according to the invention is an emulsion, in which case an oil or oily material will normally be present, together with an emulsifier to provide either a water-in-oil emulsion or an oil-in-water emulsion, depending largely on the average hydrophillic-lyophilic balance (HLB) of the emulsifier employed.

OIL OR OILY MATERIAL

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile, such as polydimethyl siloxanes.

The oil or oily material, when present for the purposes for forming an emulsion, will normally form up to 90%, preferably from 10 to 80% by volume of the composition.

EMULSIFIER

The composition according to the invention can also optionally comprise one or more emulsifiers the choice of which will normally determine whether a water-in-oil or and oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers are set below in Table 1 in which the chemical name of the emulsifiers is given together with an example of a trade name as commercially available, and the average HLB value.

TABLE 1

| Chemical Name of Emulsifier | Trade Name | HLB Value |
| --- | --- | --- |
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |

TABLE 1-continued

| Chemical Name of Emulsifier | Trade Name | HLB Value |
| --- | --- | --- |
| Poloxyethylene (2) stearyl ether | Brij 72 | 4.9 |
| Poloxyethylene sorbitol beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate | Emerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene (10) stearyl ether | Brij 76 | 12.4 |
| Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol lanolin derivative | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween | 14.9 |
| Polyoxyethylene 20 sorbitan monooleate | Tween 80 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 MS | 18.7 |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, to be incorporated in the composition of the invention, when appropriate is from 1 to 50%, preferably from 2 to 20% and most preferably from 2 to 10% by weight of the composition.

WATER

The composition of the invention can also comprise water, usually up to 98%, preferably from 5 to 80% by volume.

SILICONE SURFACTANT

The composition of the invention can also optionally comprise a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight of from 10,000 to 50,000 and having the structure:

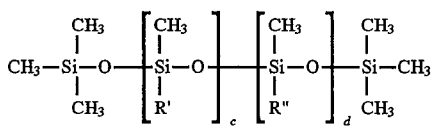

where the groups R' and R" are each chosen from —H, $C_{1-18}$ alkyl and

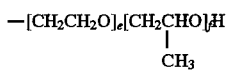

e has a value of from 9 to 115,
f has a value of from 0 to 50,
c has a value of from 133 to 673,
d has a value of from 25 to 0.25.

Preferably, the dimethyl polysiloxane polymer is one in which:
e has a value of from 10 to 114
f has a value of from 0 to 49
c has a value of from 388 to 402
d has a value of from 15 to 0.75
one of groups R' and R" being lauryl, and the other having a molecular weight of from 1000 to 5000.

A particularly preferred dimethyl polysiloxane polymer is one in which:
e has the value 14
f has the value 13
c has the value 249
d has the value 1.25

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

OTHER COSMETIC ADJUNCTS

Examples of conventional adjuncts which can optionally be employed include preservatives, such as para-hydroxy benzoate esters; antioxidants, such butyl hydroxy toluene; humectants, such as glycerol, sorbitol, 2-pyrrolidone-5-carboxylate, dibutylphthalate, gelatin, polyethylene, glycol, preferably PEG 200–600; buffers, such as lactic acid together with a base such as triethanolamine or sodium hydroxide; surfactants, such as glycerol ethers and other ceramides of synthetic, animal or plant origin; phospholipids; waxes, such as beeswax, ozokerite wax, paraffin wax, plant extracts, such as Aloe vera, cornflower, witch hazel, elderflower, cucumber; thickeners; activity enhancers; colourants; perfumes; and sunscreen materials such as ultrafine titanium dioxide and organic sunscreens such as p-aminobenzoic acid and esters thereof, ethylhexyl p-methoxycinnamate, 2-ethoxyethyl p-methoxycinnamate and butyl methoxydibenzoylmethane, and mixtures thereof.

In a further preferred composition, the phytosphingosine-containing ceramide one is combined with conventional ceramides, pseudoceramides, polyol fatty acid polyesters, sterols particularly cholesterol, galactosyldiacylglycerols, glycosphingolipids, fatty acids and esters thereof, triglycerides, cerebroside, phospholipid and other ingredients well known to those skilled in the art to produce a liposomal dispersion or bilayer structure.

A preferred composition may also contain, in combination with the phytosphingosine containing ceramide one and optional additional ingredients disclosed above, an organic acid component chosen from hydroxy carboxylic acids, keto carboxylic acids, esters thereof and mixtures thereof.

In yet another preferred composition, the phytosphingosine-containing ceramide one is dissolved in squalene or squalane, optionally together with conventional ceramides, and formulated with volatile and non-volatile silicones to produce an anhydrous or nearly anhydrous single phase system.

Cosmetic adjuncts can form the balance of the composition.

USE OF THE COMPOSITION

The composition according to the invention is intended primarily as a product for topical application to human skin, especially as an agent for reducing the permeability to water of the skin, particularly when the skin is dry or damaged, in order to reduce moisture loss and generally to enhance the quality and flexibility of skin. The composition can also be applied to hair and nails.

The composition may therefore be used as a product for topical application to human skin to treat dry, detergent-damaged or ageing skin.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

PRODUCT FORM AND PACKAGING

The topical skin, hair or nail treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer.

For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

EXAMPLES

The invention will be further described by way of illustration, in the following examples and by reference to the accompanying drawings in which:

EXAMPLE 1

Figure 1:
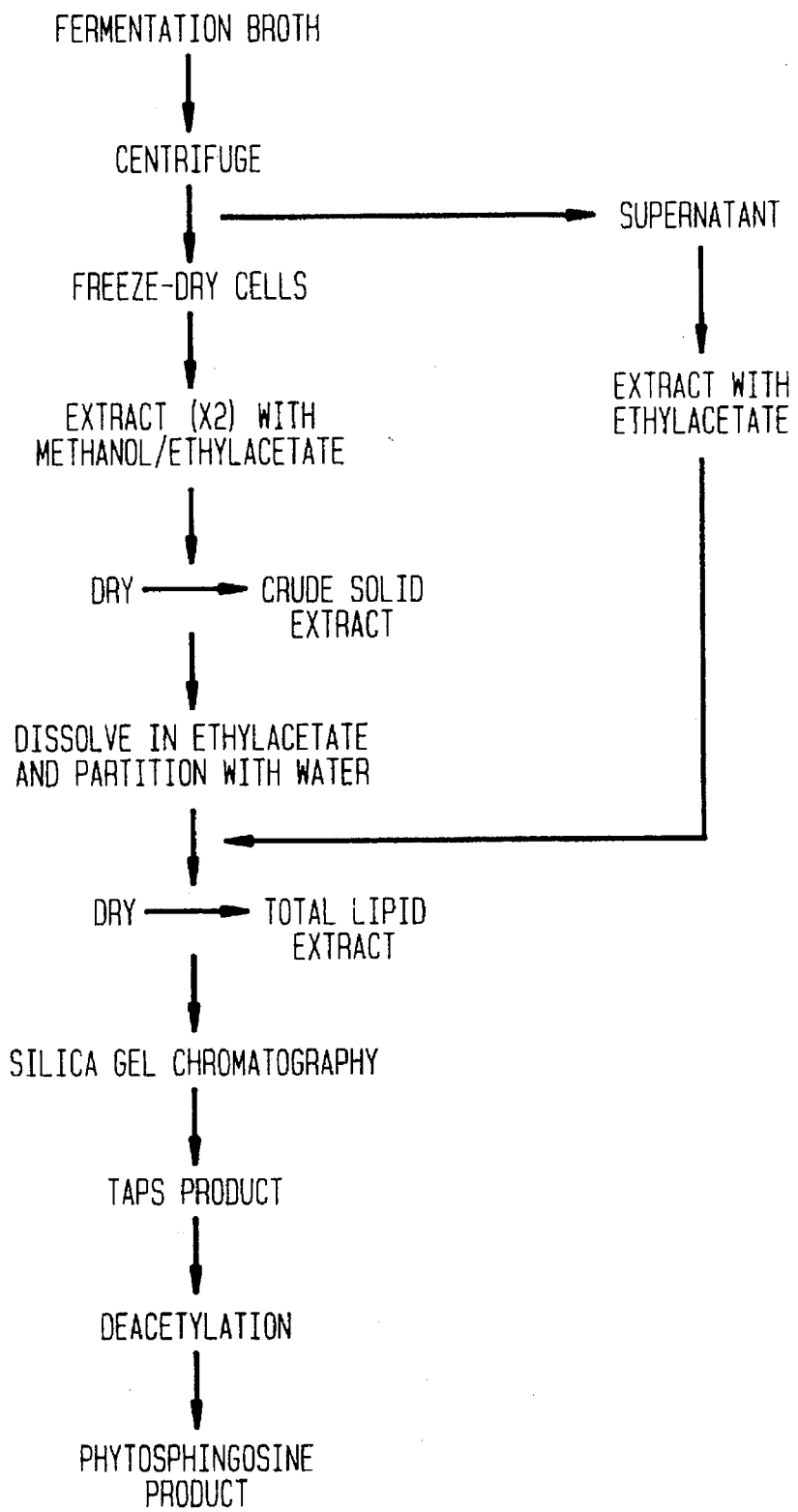
FIG. 1 is a flow chart illustrating the isolation and purification of TAPS.

Synthesis of $C_{22}$ hydroxy fatty acid from dodecanedioic acid

A solution of dodecanedioic acid (100 g) in methanol (400 ml) was reacted at 70° C. with a solution of borontrifluoride in methanol (14%, 70 ml). After 1 hour excess methanol was removed and the dioic diester product recrystallised from petroleum ether (60°–80°) (200 ml). The product was more than 99% pure in a yield of 95%.

Diester (100 g) was hydrolysed with half mole equivalent of KOH (400 ml, 90:5 methanol:water) at 70° C. for 1 hour. The reaction mix was subsequently neutralised with 1N HCl and then the aqueous phase removed by filtration. The reaction product consisting of monoester (½ acid ester), diester and diacid was dissolved in 60°–80° petroleum ether. Diacid was found to be barely soluble and was removed by filtration. The half acid ester was recrystallised twice as it was only 85% pure from one recrystallisation. The yield of half acid ester recovered pure was 52%. The reaction product was analysed by GC and IR spectroscopy. Remaining diacid, diester and impure half acid ester was recycled to give an overall yield after one recycle of 67%.

With pure half acid ester available it was possible to effect a Kolbé electrolysis to synthesise the $C_{22}$ dimethyl ester.

A solution of dodecanedioic acid half ester (10 g in 80 ml methanol) was partially neutralised with 0.1 equivalent of KOH in water (8 ml). The resulting solution was electrolysed at 120 volts and an initial current of 0.9 amps between 2 platinum electrodes 4cm×0.5cm×0.1 mm. The electrodes were set 2–3 mm apart and were constructed with a platinum/wire junction sealed in glass to isolate it from the reaction medium. On cooling to 0° C. product was found to precipitate. Reaction was carried out for 4–6 hours. The collected product was recrystallised from petroleum ether 60°–80°. The final yield of $C_{22}$ diester was 5 g (yield 60%, purity 80%) in this case.

With the long chain ester available the next step is selectively to reduce one end of the molecule. This was achieved by partial hydrolysis as before, followed by reduction of the ester moiety using lithium borohydride.

$C_{22}$ diester (1 g) was initially reacted with a half mole equivalent of KOH in methanol/water 90:10 (50 ml) at 70° C. The half acid ester was purified as before. Yield of isolated half acid ester was 300 mg (80% pure, total yield 31%).

The half ester obtained was dissolved in dry diethyl ether (5 ml) and reacted with 1 mole equivalent of lithium borohydride in dry diethyl ether (5 ml, 10% w/v). After 24 hours, reaction was stopped by addition of 1N HCl (2 ml). Diethyl ether was removed and the product washed with water and dried under vacuum. The crude mix was dissolved in ethanol (5 ml, 60° C.) and water added until turbidity was present. The $C_{22}$ product crystallised out and was filtered off. GCMS of this product showed that it was predominantly omega-hydroxy $C_{22}$ acid. Purity by GC was 74%–84%. $C^{13}$ and $H^1$ NMR also confirmed the authenticity of the product.

EXAMPLE 2

Synthesis of Phytosphingosine-containing ceramide one

Preparation of Phytosphingosine

The yeast *Hansenula* (*Pichia*) *ciferrii* (mating type F-60-10) obtained from the Northern Regional Research Labs, Peoria, Ill., USA was grown up under suitable conditions. A 1% v/v inoculum was added to the fermenter (working volume 3.5l) containing a growth medium comprising:

Glycerol, 30 gl$^{-1}$; $KH_2PO_4$, 6.4 gl$^{-1}$; $(NH_4)_2HPO_4$, 4 gl$^{-1}$; and $Na_2SO_4$, 1.5 gl$^{-1}$; together with the trace nutrients pantothenate, 6 mgl$^{-1}$; thiamine, 8 mgl$^{-1}$; nicotinic acid 30 mgl$^{-1}$; pyridoxine, 20 mgl$^{-1}$ and biotin, 100 µgl$^{-1}$. In addition some yeast extract was required, particularly to maintain cell growth during extended fermenter runs. Typically 3 gl$^{-1}$ yeast extract was added.

Fermentation was carried out at 30° C. with 0.5 v/v/min air supplied. The fermentation was characterised by the production of copious foam which was combatted by the addition of antifoam and/or by the use of a lower fermenter working volume. The course of the fermentation was continuously monitored by gas analysis, and also by glc analysis of timed samples for remaining glycerol and tetraacetylphytosphingosine (TAPS) and other metabolites produced. Additional glycerol was added at intervals, as indicated by the gas analyses, so as to maintain growth and produce as high biomass concentration as possible (greater than or equal to 50–55 gdw l$^{-1}$).

Once these high biomass concentrations were reached the broth was centrifuged at 3500 rpm at 10° C. or 20°C., and the cell pellet freeze-dried so as to facilitate solvent extraction.

ISOLATION AND PURIFICATION OF TAPS

The freeze-dried cells were ground with MeOH/EtOAc (1/1, v/v) at 60° C. and then filtered, and this extraction and filtration repeated. (85% of the TAPS was recovered in the first extraction.) The combined filtrates were evaporated under reduced pressure to produce a crude solid extract (30 g from 174 gd cells, equivalent to 690 gw cells). This solid extract was redissolved in hot EtOAc (0.5 l) and partitioned with 0.5 l of water, so as to remove water-soluble impurities; these include a sugar, probably xylitol, in significant amounts. The EtOAc phase was evaporated to dryness to produce 16.9 g of lipid extract containing alpha-HPA, cholesterol and ergosterol as metabolic side-products, plus large amounts of silicone antifoam carried over from the fermentation.

Optionally the fermentation supernatant (2.69 l) could also be extracted with EtOAc (2.5 l) to produce 1.49 g of lipid extract with a similar TAPS composition to that of the cell extract.

These extracts could be combined and dissolved in 75 ml of warm light petroleum (60°–80° C.) and chromatographed on a column of 100 g of 70–230 mesh silica gel. Elution with more petroleum (400 ml) eluted the antifoam. Elution with light petroleum –30% diethyl ether (800 ml) removed the alpha-HPA and sterols, and then finally light petroleum—60% diethyl ether (1.2 l) eluted with the TAPS in 94% yield and over 95% purity. Phytosphingosines with varying side chains, some triacetylsphingosine and also some triacetylphytosphingosine were also present.

Figure 2:
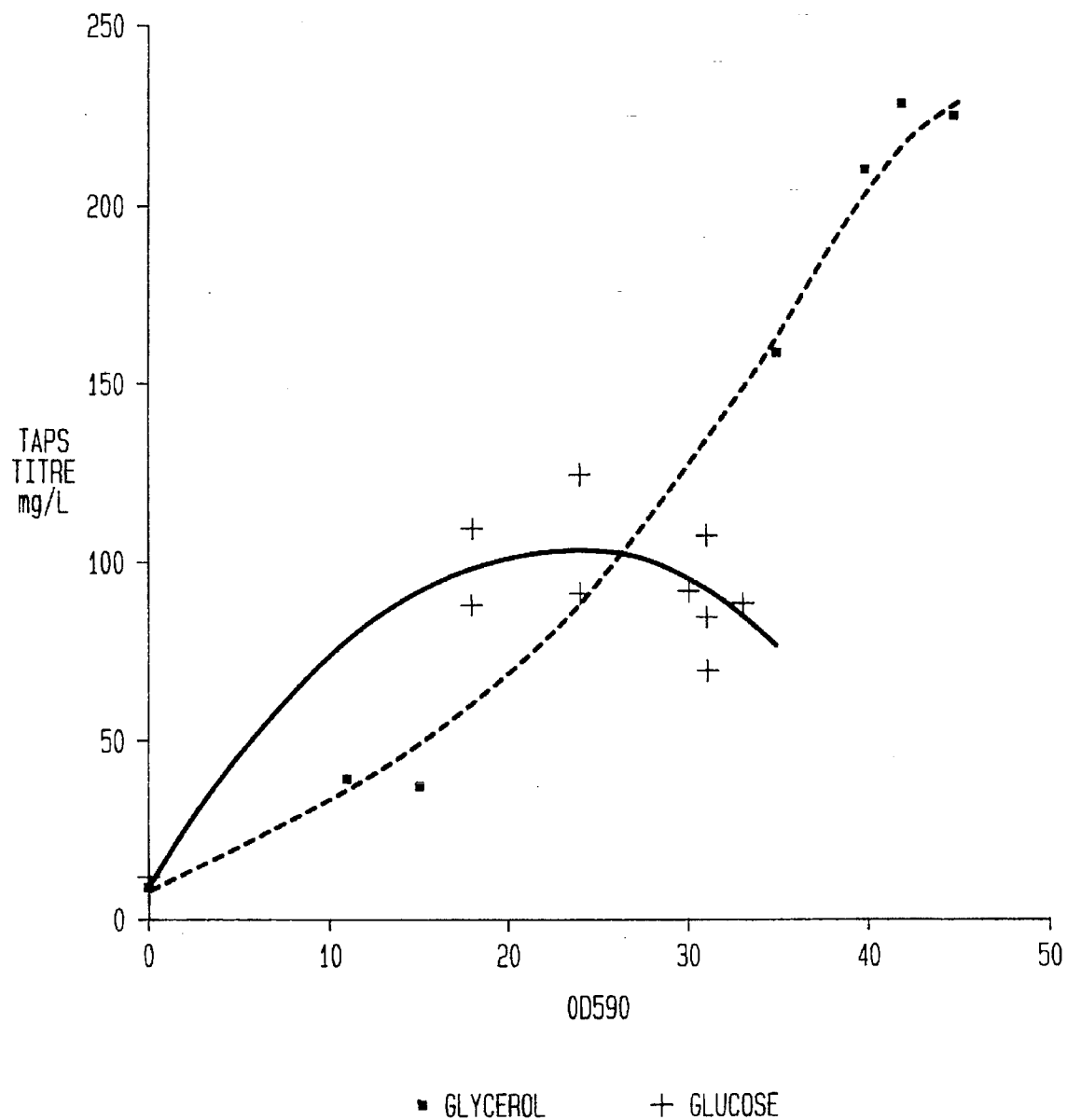
FIG. 2 and 3 are graphs of TAPS production versus increasing cell mass in a fermenter showing that TAPS formation is growth-associated, i.e. the amount of TAPS formed is directly proportional to the amount of cells grown.
Figure 3:
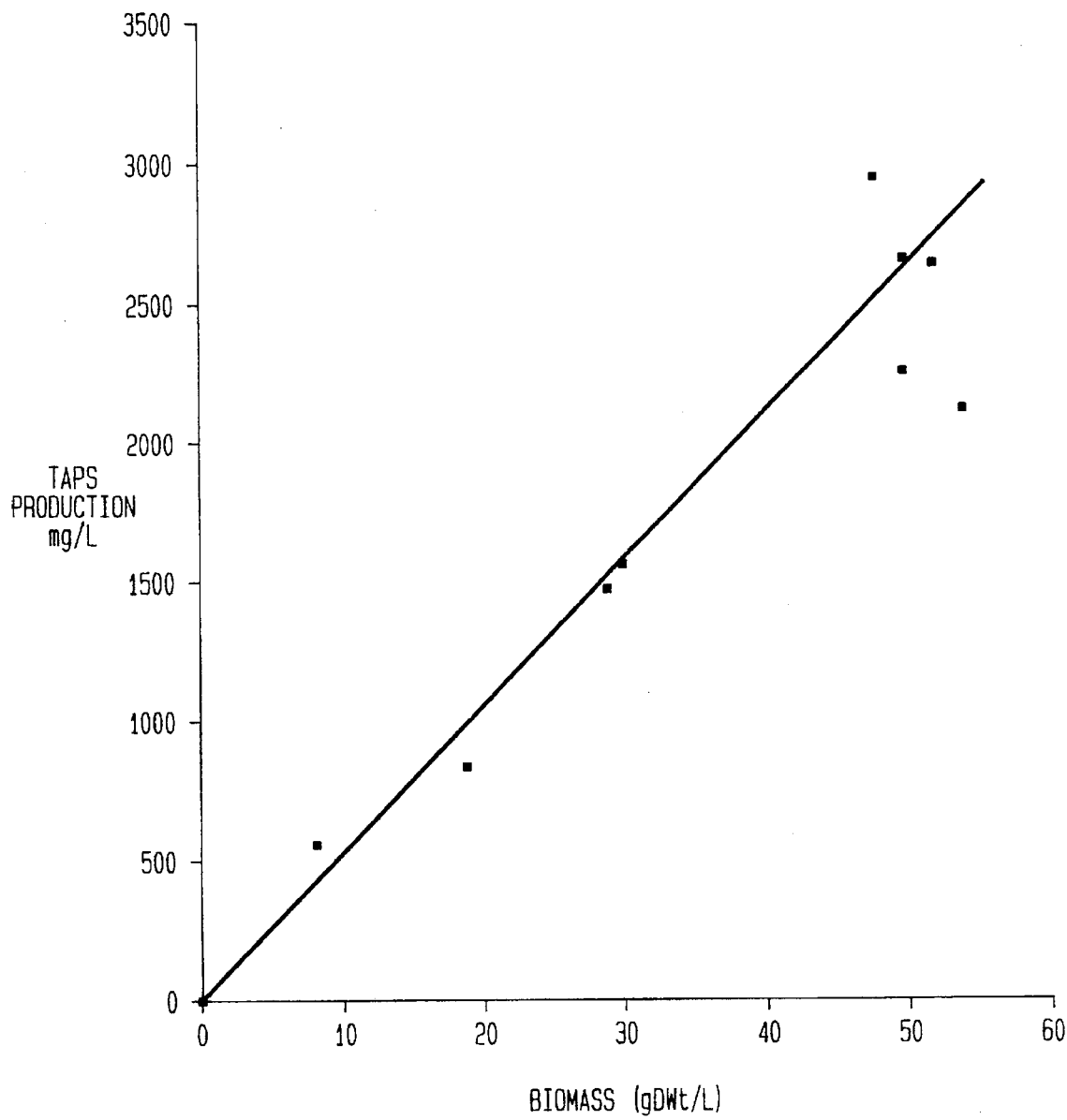
Figure 4:
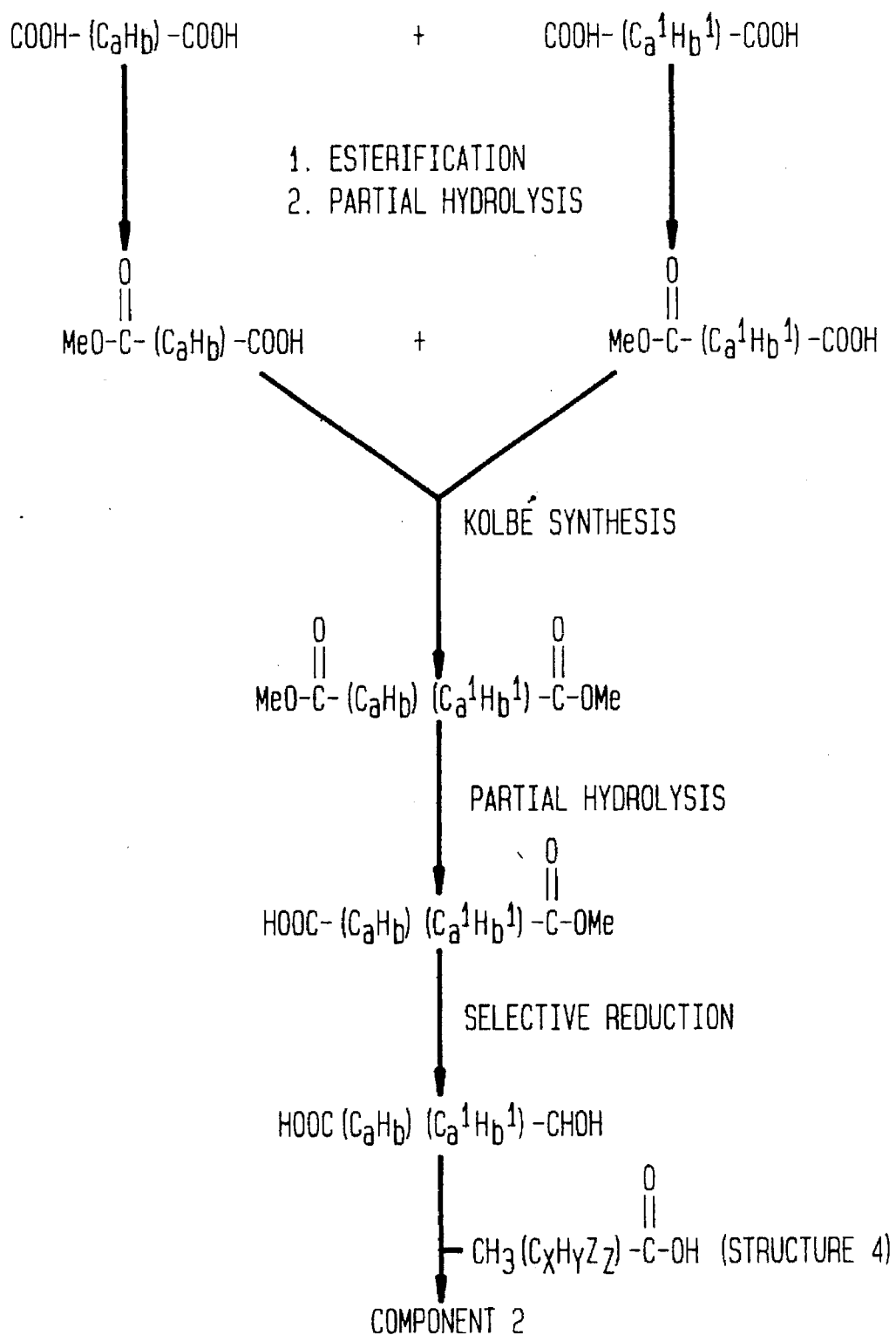
FIG. 4 illustrates the half ester route for production of component 2.
Figure 5:
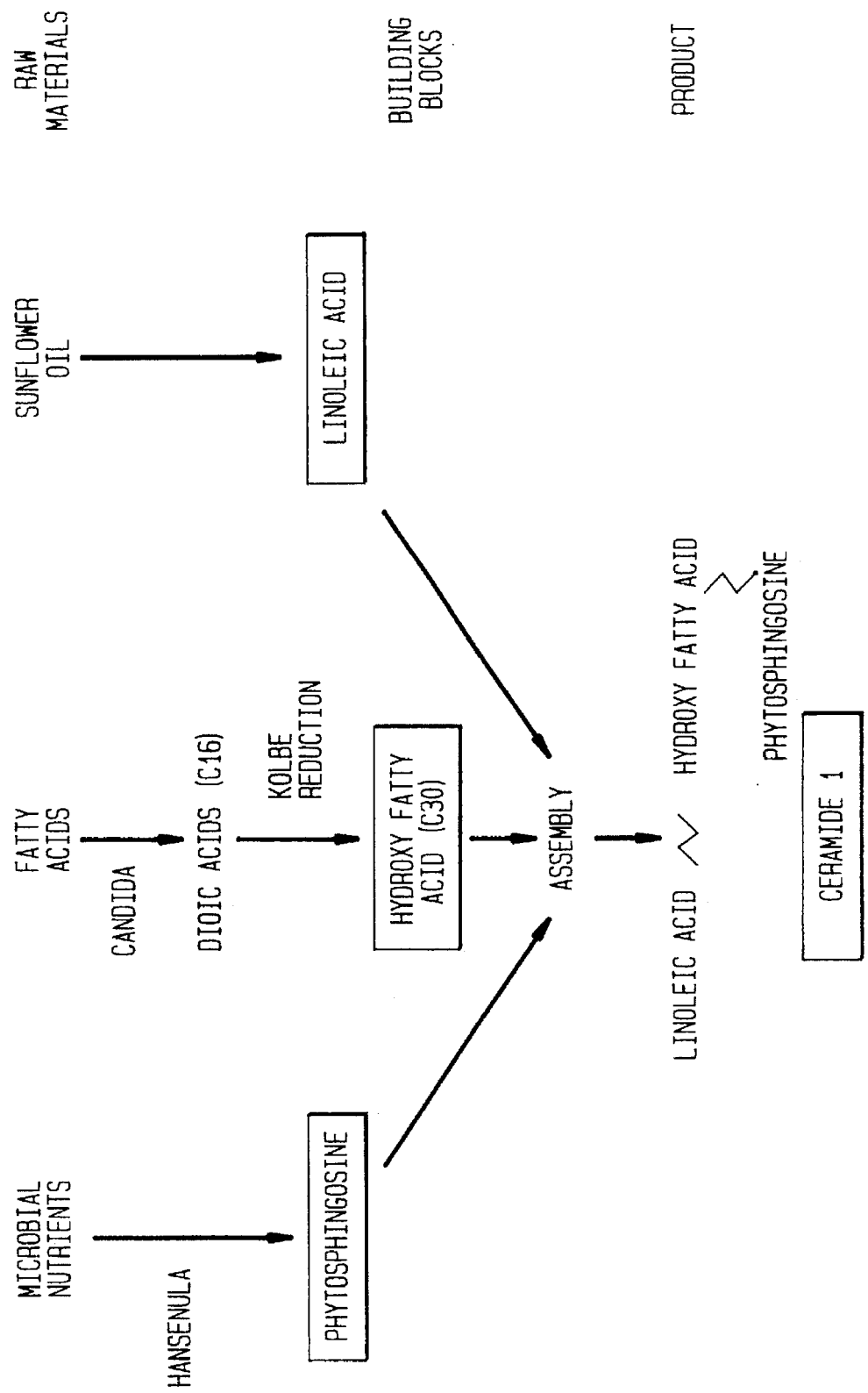
FIG. 5 illustrates schematically production of ceramide 1 by the method of the invention.

The isolation and purification of TAPS is illustrated in FIG. 1. TAPS production is illustrated graphically in FIGS. 2 and 3 including results for glycerol and glucose carbon sources. FIG. 3 gives results using glycerol only, and shows that the amount of TAPS formed is directly proportional to the amount of cells grown.

The process described is much more efficient than the prior art process. Results are shown in Tables 2 and 3.

TABLE 2

Comparison of Prior Art (Best-Case) & Present TAPS Fermentations

| | PRIOR ART | PRESENT INVENTION | |
|---|---|---|---|
| | | BATCH | FED-BATCH |
| Yield of TAPS from glucose/glycerol (mg/g) | 5 | 20 | 22 |
| Yield of TAPS on biomass (mg/gdw) | 15 | 40 | 44 |
| Max broth concentration (mgl$^{-1}$) | 307 | 600 | 2700 |
| Volumetric productivity (mg TAPS l$^{-1}$ h$^{-1}$) | 3.2* | 13.3 | 22.5 |

*Excludes 65 h post-fermentation incubation required to facilitate extraction of TAPS, otherwise 2.25 mg l$^{-1}$ h$^{-1}$.

12-hydroxydodecanoic acid (2.5 g) was dissolved in petrol 60°–80° (25 ml) and to this solution was added decanoyl chloride (2.2 g) and pyridine (1 ml). After 3 hours the reaction was stopped. The mixture was run through basic alumina II (45 g) which removed any shorter chain reactants remaining. The alumina was washed with diethyl ether. 1.5 g of product (99% by GC) was recovered (yield 35%). Confirmation of structure was by GCMS which was entirely consistent with the expected ion fragmentation pattern for the $C_{10}C_{12}$ ester.

The $C_{10}C_{12}$ acid ester (5 mg) was dissolved in dichloromethane (0.5 ml) together with phytosphingosine (4 mg) and 2-chloromethyl pyridium iodide (4 mg). To this mixture was added 5 µl triethylamine- The reaction was left at RT for 1 hour then washed 3 times with water (5 ml). The dichloromethane layer was dried over 4A molecular sieve and evaporated to dryness. The residue 9.7 mg of tan white powder was analyzed by GCMS. Yield 115%, purity 85% by GC. The major product was the $C_{10}C_{12}$ ceramide 1 as evidenced by GCMS ion fragmentation patterns.

EXAMPLE 3

This example illustrates a high internal phase water-in-oil emulsion in accordance with the invention.

A high internal phase water-in-oil emulsion having the following formulation was prepared:

TABLE 3

TAPS Fermentation Productivities

| CARBON SOURCE | TEMPERATURE (°C.) | BATCH vs FED-BATCH | TAPS TITRE (mg l$^{-1}$) | BIOMASS CONC (gdw l$^{-1}$) | SPECIFIC YIELD OF TAPS (mg/gdw cells) |
|---|---|---|---|---|---|
| Glucose | 25 | Batch | 30 | 6–8 | 6.5 |
| Glucose (pure strain of H ciferrii used) | 25 | Batch | 100 | 8.3 | 12 |
| Glycerol | 25 | Batch | 200–250 | 12 | 17–21 |
| Glycerol | 30 | Batch | 1,000 | 22 | 59 |
| Glycerol | 30 | Fed-Batch | 2,700 | 50–55 | 45–55 |
| Glycerol plus methanol | 30 | Batch | 720 | 12 | 60 |
| Glycerol plus methanol | 30 | Fed-Batch | 2083 | 34 | 61 |
| Glycerol, methanol 0.2% w/v palmitic acid 0.2% w/v serine | 30 | Batch | 1207 | 14 | 86 |

DEACETLYATION 0.9g TAPS was refluxed with 1 g KOH in ethanol/water (9/L v/v) (20 ml) for 5h. The solvent was removed under vacuum and the phytosphingosine produced extracted into diethyl ether Glc and nmr analysis showed that the phytosphingosine was obtained in 95% purity at a yield of 81%.

COUPLING PHYTOSPHINGOSINE TO COMPONENT (2)

The phytosphingosine as produced above was coupled to a fatty acid/ω-hydroxy fatty acid component (2). The component (2) was synthesised via ester formation. A broad range of types of component (2) are possible, long chain hydroxy acids being obtained as in Example 1. For ease of analysis of the final phytosphingosine-containing ceramide 1 product, in this example we synthesised a ceramide where component (2) was produced from decanoyl chloride and 12-hydroxy dodecanoic acid to give the $C_{10}C_{12}$ acid ester.

| | % w/w |
|---|---|
| Fully hydrogenated coconut oil | 3.9 |
| Phytosphingosine-containing ceramide one having the structure (5) | 0.1 |
| Brij 92* | 5 |
| Bentone 38 | 0.5 |
| Preservative | 0.3 |
| MgSO$_4$7H$_2$O | 0.3 |
| Butylated hydroxy toluene | 0.01 |
| Perfume | qs |
| Water | to 100 |

*Brij 92 is polyoxyethylene (2) oleyl ether

EXAMPLE 4

This example also illustrates a high internal phase water-in-oil emulsion in accordance with the invention in which the formulation of Example 3 was prepared but with the following changes:

i. liquid paraffin replaced the fully hydrogenated coconut oil, and ii. the phytosphingosine-containing ceramide one had the structure (6).

EXAMPLE 5

This example illustrates an oil-in-water cream emulsion having the following formulation:

|  | % w/w |
| --- | --- |
| Mineral oil | 4 |
| Phytosphingosine-containing ceramide one having the structure (7) | 0.1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 6

This example illustrates an alcoholic lotion. The lotion had the following formulation:

|  | % w/w |
| --- | --- |
| Phytosphingosine-containing ceramide one having the structure (8) | 0.2 |
| Ethanol | 40 |
| Perfume | qs |
| Butylated hydroxy toluene | 0.01 |
| Water | to 100 |

EXAMPLE 7

This example illustrates an alcoholic lotion. The lotion had the following formulation:

|  | % w/w |
| --- | --- |
| Phytosphingosine-containing ceramide one having the structure (9) | 0.2 |
| Dimethylsulphoxide | 10 |
| Ethanol | 40 |
| Antioxidant | 0.1 |
| Perfume | qs |
| Water | to 100 |

EXAMPLE 8

The following composition according to the invention represent a lotion which can be used in the treatment of dry or ageing skin:

|  | % w/w |
| --- | --- |
| Phytosphingosine-containing ceramide one having the structure (10) | 1.0 |
| Sphingosine-containing ceramide | 0.5 |
| Perfume | 0.1 |
| Hydroxyethyl cellulose | 0.4 |
| Absolute ethanol | 25 |
| p-methyl benzoate | 0.2 |
| Sterilised demineralised water | to 100 |

EXAMPLE 9

The following compositions according to the invention represent lotions which can be used in the treatment of dry or ageing skin:

|  | % w/w |
| --- | --- |
| The phytosphingosine-containing ceramide one having the structure (5) | 0.08 |
| Pseudo ceramide | 0.15 |
| Ethanol | 10 |
| Perfume | 0.5 |
| Distilled water | to 100 |

EXAMPLE 10

This example illustrates a high internal phase water-in-oil emulsion in accordance with the invention.

A high internal phase water-in-oil emulsion having the following formulation was prepared:

|  | % w/w |
| --- | --- |
| Fully hydrogenated coconut oil | 3.9 |
| Phytosphingosine-containing ceramide one having the structure (6) | 0.1 |
| Brij 92* | 5 |
| Bentone 38 | 0.5 |
| Preservative | 0.3 |
| MgSO$_4$7H$_2$O | 0.3 |
| Butylated hydroxy toluene | 0.01 |
| Perfume | qs |
| Water | to 100 |

*Brij 92 is polyoxyethylene (2) oleyl ether

EXAMPLE 11

This example also illustrates a high internal phase water-in-oil emulsion in accordance with the invention in which the formulation of Example 3 was prepared but with the following changes:

i. liquid paraffin replaced the fully hydrogenated coconut oil, and ii. the phytosphingosine-containing ceramide one had the structure (6).

EXAMPLE 12

This example illustrates an oil-in-water cream emulsion having the following formulation:

| | % w/w |
|---|---|
| Mineral oil | 4 |
| Phytosphingosine-containing ceramide one having the structure (7) | 0.05 |
| Phytosphingosine-containing ceramide one having the structure (8) | 0.05 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 13

This example illustrates an alcoholic lotion containing a phytosphingosine-containing ceramide one of the invention.

The lotion had the following formulation:

| | % w/w |
|---|---|
| Phytosphingosine-containing ceramide one having the structure (9) | 0.2 |
| Ethanol | 40 |
| Perfume | qs |
| Butylated hydroxy toluene | 0.01 |
| Water | to 100 |

EXAMPLE 14

This example illustrates an alcoholic lotion which is suitable for application to nails.

The lotion had the following formulation:

| | % w/w |
|---|---|
| Phytosphingosine-containing ceramide one having the structure (10) | 0.2 |
| Dimethylsulphoxide | 10 |
| Ethanol | 40 |
| Antioxidant | 0.1 |
| Perfume | qs |
| Water | to 100 |

EXAMPLE 15

The following composition according to the invention represent a lotion which can be used in the treatment of dry, unmanageable hair.

| | % w/w |
|---|---|
| Phytosphingosine-containing ceramide one having the structure (9) | 1.0 |
| Pseudoceramide | 0.5 |
| Perfume | 0.1 |
| Hydroxyethyl cellulose | 0.4 |
| Absolute ethanol | 25 |
| p-methyl benzoate | 0.2 |
| Sterilised demineralised water | to 100 |

EXAMPLE 16

The following compositions according to the invention represent lotions which can be used in the treatment of dry skin, hair or nails:

| | % w/w |
|---|---|
| The phytosphingosine-containing ceramide one having the structure (10) | 0.08 |
| Ethanol | 10 |
| Perfume | 0.5 |
| Distilled water | to 100 |

EXAMPLE 17

In vitro efficacy studies—water vapour transmission rate (WVTR)

$C_{30}$ linoleic phytosphingosine-containing ceramide 1 (structure 6) was prepared according to the invention. The reduction in water permeability through "Acetate Plus" membranes (from Micron Separation Inc, having 25 mm diameter and 5 μm pore size) following topical application of a composition comprising $C_{30}$ linoleic phytosphingosinecontaining ceramide was determined by in vitro measurement of the water vapour transmission rate (WVTR) using a similar system to that described by Blank et al (J Invest Dermatol 18 (1952) 433–440.

The $C_{30}$ linoleic phytosphingosine-containing ceramide was formulated in an oil in water emulsion containing cholesterol, stearic acid and sodium stearate (1:2:0.7:0.3 wt %) together with glycerol (1%) (Example 17) and compared with an identical emulsion except $C_{30}$ linoleoyl phytosphingosine-containing ceramide 1 was replaced by cholesterol (i.e. cholesterol:stearic acid and sodium stearate 3:0.7:0.3 wt % plus glycerol 1%) (comparative Example A).

Approximately 15 mgs of each aqueous formulation was applied to the membrane and allowed to dry. The membranes are weighed, and amounts of applied formulations adjusted accordingly, to ensure comparable amounts of material are applied to each membrane. Experiments are performed in triplicate.

Membranes with and without product applied are then applied to the WVTR cells with water in the wells of the cells, weighed and placed in a desiccator for 20 hours. The rate and amount of water loss is then determined from the change in weight of the diffusion cells. Barrier efficiency is demonstrated by the difference in weight loss of the treated and nontreated membranes represented as a percentage improvement in barrier efficiency.

Results are shown in Table 4.

TABLE 4

| Example | % improvement in barrier function |
|---|---|
| 17 | 9.74 ± 0.31* |
| A | 6.50 ± 0.24 |

*$P < 0.05$

We claim:

1. A method of producing a phytosphingosine-containing ceramide one having the general structure (1):

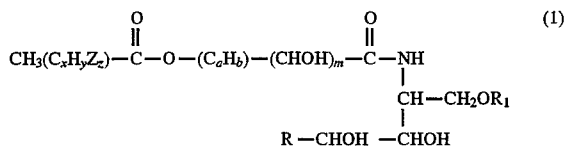

where
- R represents a linear or branched, saturated or unsaturated, hydroxylated or non-hydroxylated aliphatic hydrocarbon having from 8 to 28 carbon atoms;
- $R_1$ represents H, a phosphate residue, a sulphate residue or a sugar residue
- Z is —OH or an epoxy oxygen
- a is an integer of from 7 to 50
- b is an integer of from 10 to 100
- m is 0 or 1
- x is an integer of from 12 to 20;
- y is an integer of from 20 to 40
- z is 0 or an integer of from 1 to 4 comprising:
(a) obtaining a phytoshingosine base from tetraacetylphytosphingosine by a deacetylation reaction wherein the tetraacetylphytosphingosine. is produced by fermentation of cells of the F-60-10 mating type strain of *Hansenula ciferrii* using a fed-batch mode and a non-fermentable carbon source; and
(b) coupling together the phytosphingosine base and a fatty acid/ω-hydroxy fatty acid component having the general structure (2) via an amide linkage:

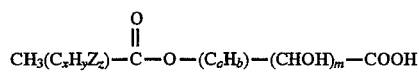

where
- Z is —OH or an epoxy oxygen
- a is an integer of from 7 to 50
- b is an integer of from 10 to 100
- m is 0 or 1
- x is an integer of from 12 to 20
- y is an integer of from 20 to 40
- z is 0 or an integer of from 1 to 4 wherein the fatty acid/ω-hydroxy fatty acid component having the general structure (2) is prepared by linking together an ω-hydroxy fatty acid having the structure (3):

and a fatty acid having the general structure (4)

2. A method according to claim 1 wherein the fermentation of cells of the F-60-10 mating type strain of *Hansenula ciferrii* (step (a)) is carried out in the presence of a solvent chosen from ethanol, methanol and mixtures thereof.

3. A method according to claim 1 wherein the fermentation of cells of the F-60-10 mating type strain of *Hansenula ciferrii* is carried out in the presence of a surfactant selected from the group consisting of Tween and Triton.

4. A method according to claim 1 wherein the of cells of the F-60-10 mating type strain of *Hansenula ciferrii* is carried using the non-fermentable carbon source glycerol.

5. A method according to claim 1 wherein the fermentation of cells of the F-60-10 mating type strain of *Hansenula ciferrii* is carried out in the presence of a tetraacetylphytosphingosine precursor selected from the group consisting of palmitic acid, serine and mixtures thereof.

6. A method according to claim 1 wherein the fermentation of cells of the F-60-10 mating type strain of *Hansenula ciferrii* is carried out at 30° C.

7. A method according to claim 1 wherein the phytosphingosine base and component (2) are linked by chemical or enzymatic routes.

* * * * *